| United States Patent [19] | [11] Patent Number: 5,041,643 |
|---|---|
| Tinti et al. | [45] Date of Patent: Aug. 20, 1991 |

[54] PROCESS FOR THE PRODUCTION OF R(+)-AMINOCARNITINE AND S(−)-AMINOCARNITINE

[75] Inventors: Maria O. Tinti; Domenico Misiti, both of Rome, Italy

[73] Assignee: Sigma-Tau Industrie Farmaceutiche Riunite S.p.A., Rome, Italy

[21] Appl. No.: 506,823

[22] Filed: Apr. 10, 1990

[30] Foreign Application Priority Data

Apr. 12, 1989 [IT] Italy .................... 47842 A/89

[51] Int. Cl.$^5$ .................................... C07C 227/18
[52] U.S. Cl. .................... 562/561; 560/172; 560/169; 560/38
[58] Field of Search .................... 560/172, 169, 38; 562/561

[56] References Cited

U.S. PATENT DOCUMENTS

| 4,521,432 | 6/1985 | Kanamaru et al. | 562/561 |
| 4,767,781 | 8/1988 | Shinagawa et al. | 562/561 |
| 4,781,863 | 11/1988 | Griffith | 562/561 |

Primary Examiner—James H. Reamer
Attorney, Agent, or Firm—Oblon, Spivak, McClelland, Maier & Neustadt

[57] ABSTRACT

A process for the production of R(+)-aminocarnitine and S(−)-aminocarnitine is disclosed by resolution of the mixture of the diastereoisomers of N-(alpha-methylbenzyl) aminocarnitine benzyl ester chloride, wherein the separated diastereoisomers are subsequently debenzylated to give R(+)-aminocarnitine chloride and S(−)-aminocarnitine chloride.

4 Claims, No Drawings

PROCESS FOR THE PRODUCTION OF R(+)-AMINOCARNITINE AND S(−)-AMINOCARNITINE

The present invention relates to a process for the production of R(+)-aminocarnitine and S(−)-aminocarnitine, by chromatographic separation on a silica gel column or fractional crystallisation of a mixture of diastereoisomers consisting of the benzyl esters of N-[S(−) alpha-methylbenzyl]-R(+)-aminocarnitine chloride and N-[S(−) alpha-methylbenzyl]-S(−)-aminocarnitine chloride, or a mixture of diastereoisomers consisting of the benzyl esters of N-[R(+) alpha-methylbenzyl]-R(+)-aminocarnitine chloride and N-[R(+) alpha-methylbenzyl]-S(−)-aminocarnitine chloride, followed by debenzylation of the separated diastereoisomers to yield R(+)-aminocarnitine chloride and S(−)-aminocarnitine chloride.

Recently, the discovery of pharmacological properties of aminocarnitine (I,R=H) and certain acyl derivatives of aminocarnitine (I,R=acetyl, N-caproyl, palmitoyl) has aroused substantial interest.

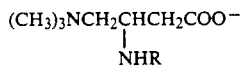
(I)

For example, D. L. Jenkins and O. W. Griffith have described antiketogenic and hypoglycemic effects of compounds (I) in their racemic form. Also, U.S. Pat. No. 4,521,432 (Takeda) describes the antiketogenic activity (with the accompanying possibility of applications in the treatment of diabetes) of an optically active derivative, (−)-N-acetyl aminocarnitine, inner salt ($[\alpha]_D^{25} = -17.4°$, c=1, H$_2$O). Analogous activity has been described for (+)-aminocarnitine chloride hydrochloride ($[\alpha]_D^{25} = +6.3°$, c=1, 1N AcOH).

Therefore, we feel that it is necessary to have available a process that provides both enantiomeric forms of aminocarnitine.

Actually, R(+)-aminocarnitine chloride can be obtained by acid hydrolisis of R(−)-N-acetyl aminocarnitine, isolated as a product during the cultivation of microorganisms of the genera Emericella or Aspergillus, or via a complex chemical procedure as described in the aforecited U.S. Pat. No. 4,521,432 (Takeda).

The synthesis of R(+)- and S(−)-aminocarnitine chloride starting from L- and from D-asparagine was described by Schinagawa in J. Med. Chem., 30:1458 (1987). However, this synthetic method is rather complex. Indeed, it includes seven steps and involves the use of particularly dangerous reagents, such as diazomethane. Therefore, it is not a method suitable for industrial production, and was of value only insofar as it permitted assignment of the absolute configurations of (+)-aminocarnitine and (−)-aminocarnitine as R-aminocarnitine and S-aminocarnitine, respectively.

R-aminocarnitine chloride and S-aminocarnitine chloride can also be obtained by resolution of a racemic mixture of (±)-N-acetyl aminocarnitine, as described in SIGMA-TAU's Italian patent application 47738/87 (Italian patent 1,205,758 corresponding to EP application 287,523). However, in this case the starting material, (±)-N-acetyl aminocarnitine, was synthesized as described by D. Jenkins in J. Biol. Chem., 260: 14748 (1985), using a rather complex five-step procedure starting with a uracil derivative.

The object of the present invention is to provide a process for the production of R(+)-aminocarnitine and S(−)-aminocarnitine that does not entail the drawbacks of the prior art processes. In particular, the process of the present invention allows for the preparation of both enantiomers in good yields, utilising as the starting material a substance like crotonobetaine which is inexpensive and readily obtained by the dehydration of D-carnitine (a side product obtained during the preparation of L-carnitine).

To the benzylic ester of crotonobetaine chloride is added one of the two enantiomers of alpha-methylbenzylamine. Since it forms a new chiral centre, and since the addition is not stereospecific, both possible diastereoisomers are obtained. If R(+) alpha-methylbenzylamine is used, one obtains the benzyl esters of N-[R(+) alpha-methylbenzyl]R(+)-aminocarnitine chloride and N-[R(+) alpha-methylbenzyl]-S(−)-aminocarnitine chloride; whereas if S(−) alpha-methylbenzylamine is employed, the benzyl esters of N-[S(−) alpha-methylbenzyl]-R(+)-aminocarnitine chloride and N-[S(−) alpha-methylbenzyl]-S(−)-aminocarnitine chloride are obtained.

In either of these cases, it is possible to separate the diastereoisomers either by fractional crystallisation or by chromatography on silica gel. The separated diastereoisomers are then catalytically hydrogenated to simultaneously remove the N- and O-benzyl groups, yielding in a single step the final product: R(+)-aminocarnitine chloride or S(−)-aminocarnitine chloride.

In accordance with the process of the present invention, R(+)- and S(−)-aminocarnitine chloride are prepared as per the following synthesis scheme (scheme I):

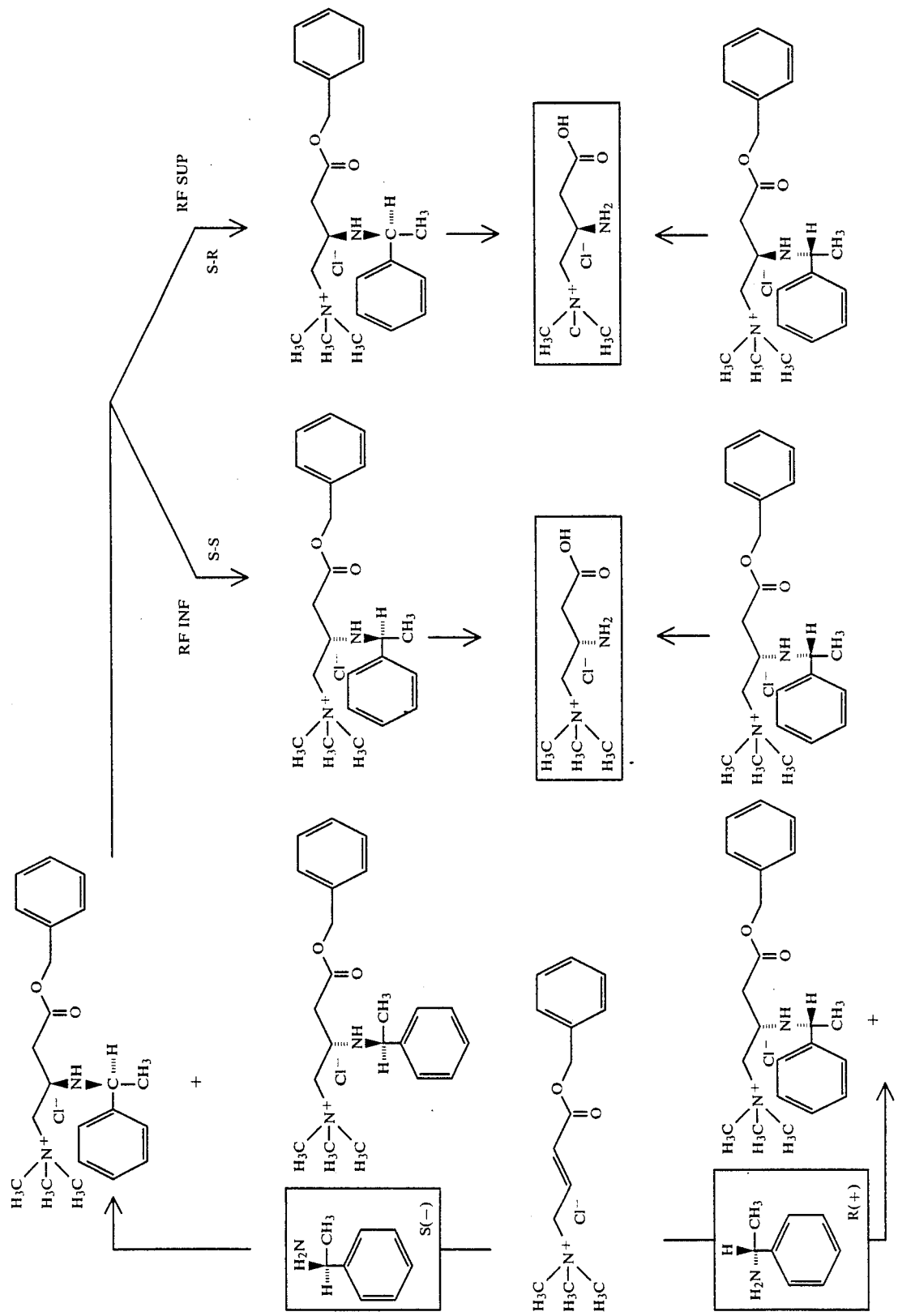

-continued
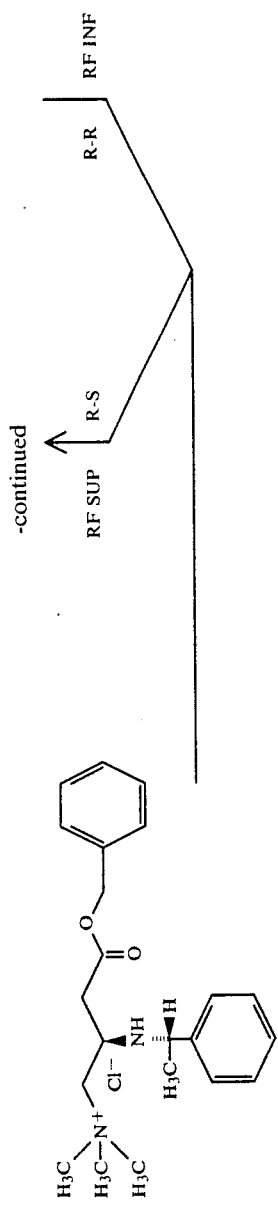

More particularly, the process of the present invention comprises the steps of:

(a) reacting crotonobetaine chloride with an excess amount of benzyl alcohol in the presence of an acid catalyst such as gaseous hydrochloric acid or thionyl chloride, concentrating the resulting reaction solution, thus isolating crotonobetaine benzylester chloride;

(b) reacting crotonobetaine benzyl ester chloride with an excess amount of R or S alpha-methylbenzylamine, at 10° C.-30° C., for 12-48 hours and isolating N-(alpha-methylbenzyl) aminocarnitine benzylester chloride from the resulting reaction mixture by precipitation with an organic solvent such as ethyl ether or acetonitrile;

(c) resolving the thus formed diastereoisomers, preferably by fractional crystallisation with acetone or methylethylketone or by chromatography on a silica gel column using a gradient of chloroform-methanol as eluant;

(d) subjecting each diastereoisomer to hydrogenolysis in a hydroalcoholic solution in the presence of a hydrogenation catalyst selected from the group consisting of palladium hydroxide and pallaium chloride and isolating R(+) and S(−)-aminocarnitine chloride; and (e) converting the aminocarnitine enantiomers obtained in the previous step to chlorides hydrochlorides with hydrochloric acid.

The process of the present invention is illustrated by the following non-limiting example.

STEP A

Preparation of crotonobetaine benzylester chloride 54 ml benzyl alcohol were added to crotonobetaine (15 g; 0.083 moles). The resulting mixture was cooled to 0° C. Thionyl chloride (35 ml; 0.495 moles) was slowly added to the mixture. The mixture was then kept at room temperature for 16 hours. Subsequently, the solution was concentrated under vacuum in order to remove the excess thionyl chloride. The residue was washed with isopropanol, concentrated under vacuum and taken up with acetone. The acetone solution was kept overnight at 4° C. A precipitate was obtained (19 g; yield 84%) which was filtered and dried. The analysis showed that the resulting compound was the title compound.

TLC silica gel, eluant: chloroform: methanol: isopropanol: $H_2O$: acetic acid (42:28:7:10:10), RF=0.7.

NMR $D_2O$ δ7.5 (5H, s, aromatic); 7.2-6.3(2H, m, CH=CH); 5.2(2H, s,

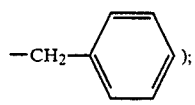

4.2(2H, d, $N^+$—$CH_2$); 3.0(9H, s, $(CH_3)_3N^+$), Melting point = 78°-80° C.,

STEP B

Preparation of N-(alpha-methylbenzyl) aminocarnitine benzyl ester chloride

R(+) alpha-methylbenzylamine (47 ml; 0.37 moles) was added to crotonobetaine benzylester chloride (26 g; 0.096 moles). The resulting solution was kept under stirring at room temperature for 24 hours. Ethyl ether was added to the solution giving a precipitate (33 g; yield 87.5%). TLC silica gel, eluant: chloroform-methanol (80-20)

The reaction raw material consisted of a mixture of the two diastereoisomers N-(R(+) alpha-methylbenzyl) R(+)-amino-carnitine benzylester chloride; inferior RF=0.6; and N-(R(+) alpha-methylbenzyl) S(−)-aminocarnitine benzyl ester chloride superior RF=0.8.

NMR $D_2O$ δ7.1 (10H, duplet s, aromatic); 5.0(2H, s,

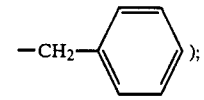

4.0-3.8 (2H, m, —CH—$CH_3$; CH—NH); 3.4(2H, m, $N^+$—$CH_2$); 3.2(9H, s, $(CH_3)_3N^+$); 2.8(2H, m, —$CH_2$COO—); 1.2(3H, d, —CH—$CH_3$),

STEP C

Resolution of diastereoisomers

The reaction raw material was dissolved in chloroform and eluted through a silica gel column (ratio 1:20), eluant: chloroform-methanol (95-5).

The following compounds were isolated:
product at inferior RF:N-(R(+)alpha-methylbenzyl) R(+)-aminocarnitine benzyl ester chloride
$[\alpha]_D^{25} = -12$ (c=1, $H_2O$).
melting point: 176°-178° C.,
HPLC: column Tekopac $C_{18}$ eluant: Solvent A-$CH_3CN$ (58-42) (solvent A: methanol 100 ml+85% $H_3PO_4$ 3 ml+$H_2O$ balance to 1000 ml).
detector UV 205 nm.
flow rate: 1 ml/min.
retention time: 6.69 min.
title: 95%.

product at superior RF: N-(R(+)alpha-methylbenzyl) S(−)-aminocarnitine benzyl ester chloride.
$[\alpha]_D^{25} = +52.6$ (c=1, $H_2O$).
melting point: 60°-62° C.,
HPLC: as above.
retention time: 8.28 min.
title: 90%.

| Elementary analysis: $(C_{22}H_3,N_2ClO_2)$ | | | |
|---|---|---|---|
| C%, | H%, | N%, | Cl% |
| calc: 67.58; | 7.99; | 7.16; | 9.06; |
| found: 67.52; | 8.02; | 7.09, | 9.13. |

The separation of the diastereoisomers was also obtained by crystallisation with methylethylketone that gave the compound at inferior RF with 80% purity, while the compound at superior RF remained in the mother liquors.

STEP D

Preparation of R(+)-aminocarnitine chloride

The compound at inferior RF of step C, viz. N-(R(+)alpha-methylbenzyl)R(+)-aminocarnitine benzyl ester (1 g; 0.0025 moles) was dissolved in 10 ml ethanol-$H_2O$, ratio 1:1. To the resulting solution 500 mg Pd(OH)$_2$ were added. The solution was hydrogenated at 4 atmospheres overnight. The catalyst was then filtered off and the resulting solution concentrated under vacuum.

The residue was washed with isopropanol and the solid thus obtained was filtered off.

0.5 g of a crystalline compound were obtained.
yield: 100%.
$[\alpha]_D^{25} = +12$ (c=1, H$_2$O).

Determination of the enantiomeric excess of R(+)-aminocarnitine chloride hydrochloride.

Aminocarnitine was derivatized with orthophtalic aldehyde and acetylcysteine according to a method used for the determination of aminoacid enantiomeric excess described in An. Chem. 51(11), 1667, 1979, as illustrated in scheme 2.

SCHEME 2
Derivatization of (+)-aminocarnitine

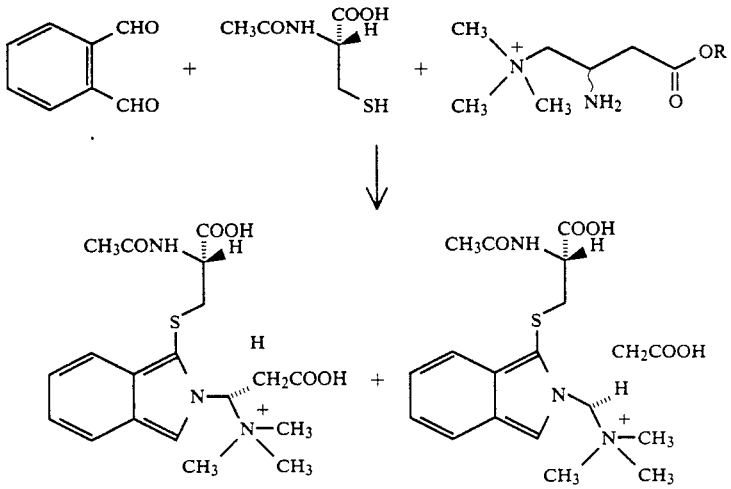

melting point: 194°–196° C.

| Elementary analysis: (C$_7$H$_{17}$N$_2$ClO$_2$) | | | |
|---|---|---|---|
| | C% | H% | N% | Cl% |
| calc: | 42.74; | 8.71; | 14.23; | 18.02 |
| found: | 41.74; | 9.08; | 13.35; | 18.04 |

STEP E

Preparation of R(+)-aminocarnitine chloride hydrochloride

In order to compare the chemico-physical data of aminocarnitine chloride with those disclosed in the chemical literature, R(+)-aminocarnitine chloride was treated with acqueous HCl until pH 1.8 was reached, and then lyophilized. A solid product was obtained.
$[\alpha]_D^{25} = +7$(C=1, H$_2$O).
melting point: 210°–212° C.

| Elementary analysis: C$_7$H$_{18}$N$_2$Cl$_2$O$_2$ | | | |
|---|---|---|---|
| | C% | H% | N% | Cl% |
| calc: | 36.06; | 7.78; | 12.01; | 30.41 |
| found: | 35.70; | 7.84; | 11.50; | 29.78 |

NMR D$_2$O δ4.2(1H, m-C<u>H</u>); 
|
N 3.8(2H, d, N+CH$_2$—); 3.2(9H, s, (CH$_3$)$_3$N+—); 2.8(2H, d, —CH$_2$COO−).

HPLC: column micro Bondapack C$_{18}$: eluant: KH$_2$PO$_4$ 0.05 M-CH$_3$CN(35–65); detector UV 205 nm; flow rate: 1 ml/min; retention time: 20.3 min.

The derivatized mixture was analyzed via HPLC.
Column micro Bondapack C$_{18}$.
eluant: NaClO$_4$0.05M: CH$_3$CN(97:3).
detector UV 336 nm.
flow rate: 1 ml/min.
95% R(+)-aminocarnitine retention time: 17.5 min.
5% S(−)-aminocarnitine retention time: 20.6 min.

What is claimed is:

1. A process for producing R(+)-aminocarnitine and S(−)-aminocarnitine which comprises the steps of:
   A) reacting crotonobetaine chloride with an excess amount of benzyl alcohol in the presence of an acid catalyst selected from the group consisting of gaseous hydrochloric acid and thionyl chloride, and concentrating the resulting reaction solution, thus isolating crotonobetaine benzyl ester chloride;
   B) reacting crotonobetaine benzyl ester chloride with an excess amount of R and S alpha-methylbenzylamine, at 10° C.–30°C., for 12–48 hours and isolating N-(alpha-methylbenzyl) aminocarnitine benzylester chloride from the resulting reaction mixture by precipitation with an organic solvent selected from the group consisting of ethyl ether and acetonitrile;
   C) resolving the thus formed diastereoisomers by fractional crystallization with acetone or methylethylketone or by chromatography on a silica gel column using a gradient chloroform-methanol as eluant;
   D) subjecting each diastereoisomer to hydrogenolysis in a hydroalcoholic solution in the presence of a hydrogenation catalyst selected from the group consisting of palladium hydroxide and palladium chloride and isolating R(+) and S(−)-aminocarnitine chloride; and E) converting the aminocarnitine enantiomers obtained in the previous step to chlorides hydrochlorides with hydrochloric acid.

2. The process of claim 1, wherein the excess amount of benzyl alcohol to crotonobetaine chloride is about 6:1 expressed as a molar ratio.

3. The process of claim 1, wherein the excess amount of R or S alpha-methylbenzylamine is about 4:1 expressed as a molar ratio.

4. The process of claim 1, wherein hydrogenolysis is conducted at a pressure of 4 atmospheres.

* * * * *